(12) United States Patent
Landry et al.

(10) Patent No.: US 9,017,419 B1
(45) Date of Patent: Apr. 28, 2015

(54) LINEAR ACTUATOR

(71) Applicant: Össur hf, Reykjavik (IS)

(72) Inventors: David Landry, Quebec (CA); Bjarni Andresson, Seltjarnarnes (IS)

(73) Assignee: Össur hf, Reykjavik (IS)

( * ) Notice: Subject to any disclaimer, the term of this patent is extended or adjusted under 35 U.S.C. 154(b) by 125 days.

(21) Appl. No.: 13/790,184

(22) Filed: Mar. 8, 2013

Related U.S. Application Data

(60) Provisional application No. 61/609,080, filed on Mar. 9, 2012.

(51) Int. Cl.
    *A61F 2/48*     (2006.01)
    *H02K 7/10*     (2006.01)
    *A61F 2/66*     (2006.01)

(52) U.S. Cl.
CPC ... *H02K 7/10* (2013.01); *A61F 2/66* (2013.01)

(58) Field of Classification Search
CPC .................. A61F 2002/6607; A61F 2002/701
USPC ............ 623/24, 39, 40, 50; 310/49.08, 49.09; 74/89.23, 89.28, 89.35
See application file for complete search history.

(56) References Cited

U.S. PATENT DOCUMENTS

| | | |
|---|---|---|
| 1,951,622 A | 3/1934 | McElroy |
| 2,568,051 A | 9/1951 | Catranis |
| 2,660,029 A | 11/1953 | Geyer |
| 2,930,659 A | 3/1960 | Willmore |
| 3,022,400 A | 2/1962 | von Ahlefeldt |
| 3,229,545 A | 1/1966 | Hautau |
| 3,579,276 A | 5/1971 | Newell |
| 3,678,311 A | 7/1972 | Mattingly |
| 3,803,926 A | 4/1974 | Winter |
| 3,820,168 A | 6/1974 | Horvath |
| 3,995,324 A | 12/1976 | Burch |
| 4,030,141 A | 6/1977 | Graupe |

(Continued)

FOREIGN PATENT DOCUMENTS

| | | |
|---|---|---|
| EP | 0 902 547 | 3/1999 |
| EP | 1 107 420 | 6/2001 |

(Continued)

OTHER PUBLICATIONS

Au S K et al., "An EMG-Position Controlled System for an Active Ankle-Foot Prosthesis: An Initial Experimental Study" Rehabilitation Robotics, 2005. ICORR 2005., 9th International Conference in Chicago, IL, USA Jun. 28-Jul. 1, 2005, Piscataway, NJ, IEEE, Jun. 28, 2005, pp. 375-379, XP008078417.

(Continued)

*Primary Examiner* — Bruce E Snow
(74) *Attorney, Agent, or Firm* — Knobbe, Martens, Olson & Bear, LLP.

(57) ABSTRACT

Linear actuators that allow for improved self-locking properties without sacrificing axial response are provided. A linear actuator can have two screws extending from opposite ends of the actuator. The screws are joined by and threadably coupled to an elongate rotating nut. An elongate magnet is disposed around and coupled to the nut, and a stator including coils surrounds the magnet and nut. The magnet and nut are not axially fixed with respect to the stator. Rotation of the nut causes axial displacement of both screws, causing the screws to move closer together or farther apart. A pitch of the screw threads can be selected to enhance self-locking properties.

16 Claims, 14 Drawing Sheets

(56) References Cited

U.S. PATENT DOCUMENTS

| | | |
|---|---|---|
| 4,065,815 A | 1/1978 | Sen-Jung |
| 4,094,086 A | 6/1978 | Edwards |
| 4,152,787 A | 5/1979 | Meggyesy |
| 4,179,759 A | 12/1979 | Smith |
| 4,209,860 A | 7/1980 | Graupe |
| 4,212,087 A | 7/1980 | Mortensen |
| 4,387,472 A | 6/1983 | Wilson |
| 4,398,109 A | 8/1983 | Kuwako et al. |
| 4,420,714 A | 12/1983 | Petersen et al. |
| 4,501,981 A | 2/1985 | Hansen |
| 4,521,924 A | 6/1985 | Jacobsen et al. |
| 4,558,704 A | 12/1985 | Petrofsky |
| 4,569,352 A | 2/1986 | Petrofsky et al. |
| 4,711,242 A | 12/1987 | Petrofsky |
| 4,776,852 A | 10/1988 | Rubic |
| 4,876,944 A | 10/1989 | Wilson et al. |
| 4,892,554 A | 1/1990 | Robinson |
| 4,944,755 A | 7/1990 | Hennequin et al. |
| 4,994,086 A | 2/1991 | Edwards et al. |
| 5,044,360 A | 9/1991 | Janke |
| 5,062,856 A | 11/1991 | Sawamura et al. |
| 5,062,857 A | 11/1991 | Berrigner |
| 5,092,902 A | 3/1992 | Adams et al. |
| 5,112,296 A | 5/1992 | Beard et al. |
| 5,112,356 A | 5/1992 | Harris et al. |
| 5,133,773 A | 7/1992 | Sawamura et al. |
| 5,133,774 A | 7/1992 | Sawamura et al. |
| 5,139,525 A | 8/1992 | Kristinsson |
| 5,153,496 A | 10/1992 | LaForge |
| 5,181,931 A | 1/1993 | Van de Veen |
| 5,201,772 A | 4/1993 | Maxwell |
| 5,217,500 A | 6/1993 | Phillips |
| 5,219,365 A | 6/1993 | Sabolich |
| 5,252,102 A | 10/1993 | Singer et al. |
| 5,336,269 A | 8/1994 | Smits |
| 5,376,133 A | 12/1994 | Gramnäs |
| 5,376,137 A | 12/1994 | Shorter et al. |
| 5,383,939 A | 1/1995 | James |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,443,521 A | 8/1995 | Knoth et al. |
| 5,443,524 A | 8/1995 | Sawamura et al. |
| 5,443,528 A | 8/1995 | Allen |
| 5,466,083 A | 11/1995 | Hogg |
| 5,472,412 A | 12/1995 | Knoth |
| 5,476,441 A | 12/1995 | Durfee et al. |
| 5,504,415 A | 4/1996 | Podrazhansky et al. |
| 5,545,232 A | 8/1996 | Van de Veen |
| 5,545,233 A | 8/1996 | Fitzlaff |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,586,557 A | 12/1996 | Nelson et al. |
| 5,611,508 A | 3/1997 | Palmero |
| 5,650,704 A | 7/1997 | Pratt et al. |
| 5,656,915 A | 8/1997 | Eaves |
| 5,662,693 A | 9/1997 | Johnson et al. |
| 5,704,945 A | 1/1998 | Wagner et al. |
| 5,704,946 A | 1/1998 | Greene |
| 5,728,170 A | 3/1998 | Becker et al. |
| 5,746,774 A | 5/1998 | Kramer et al. |
| 5,751,083 A | 5/1998 | Tamura et al. |
| 5,779,735 A | 7/1998 | Molino |
| 5,800,568 A | 9/1998 | Atkinson et al. |
| 5,888,212 A | 3/1999 | Petrofsky et al. |
| 5,888,213 A | 3/1999 | Sears et al. |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Connor |
| 5,919,149 A | 7/1999 | Allum |
| 5,955,667 A | 9/1999 | Fyfe |
| 5,957,981 A | 9/1999 | Gramnäs |
| 5,972,035 A | 10/1999 | Blatchford |
| 5,982,156 A | 11/1999 | Weimer et al. |
| 5,998,930 A | 12/1999 | Upadhyay et al. |
| 6,007,582 A | 12/1999 | May |
| 6,061,577 A | 5/2000 | Andrieu et al. |
| 6,091,977 A | 7/2000 | Tarjan et al. |
| 6,113,642 A | 9/2000 | Petrofsky et al. |
| 6,129,766 A | 10/2000 | Johnson et al. |
| 6,164,967 A | 12/2000 | Sale et al. |
| 6,165,226 A | 12/2000 | Wagner |
| 6,183,425 B1 | 2/2001 | Whalen et al. |
| 6,187,051 B1 | 2/2001 | Van de Veen |
| 6,195,921 B1 | 3/2001 | Truong |
| 6,206,932 B1 | 3/2001 | Johnson |
| 6,206,934 B1 | 3/2001 | Phillips |
| 6,241,775 B1 | 6/2001 | Blatchford |
| 6,301,964 B1 | 10/2001 | Fyfe et al. |
| 6,350,286 B1 | 2/2002 | Atkinson et al. |
| 6,361,570 B1 | 3/2002 | Gow |
| 6,373,152 B1 | 4/2002 | Wang et al. |
| 6,409,695 B1 | 6/2002 | Connelly |
| 6,423,098 B1 | 7/2002 | Biedermann |
| 6,425,925 B1 | 7/2002 | Grundei |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,537,322 B1 | 3/2003 | Johnson et al. |
| 6,602,295 B1 | 8/2003 | Doddroe et al. |
| 6,610,101 B2 | 8/2003 | Herr et al. |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,719,806 B1 | 4/2004 | Zahedi et al. |
| 6,740,123 B2 | 5/2004 | Davalli et al. |
| 6,743,260 B2 | 6/2004 | Townsend |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,770,045 B2 | 8/2004 | Naft et al. |
| 6,876,135 B2 | 4/2005 | Pelrine |
| 6,955,692 B2 | 10/2005 | Grundei |
| 6,966,933 B2 | 11/2005 | Christensen |
| 7,029,500 B2 | 4/2006 | Martin |
| 7,063,727 B2 | 6/2006 | Phillips et al. |
| 7,091,679 B2 | 8/2006 | Schroeder et al. |
| 7,118,601 B2 | 10/2006 | Yasui |
| 7,131,998 B2 | 11/2006 | Pasolini |
| 7,137,998 B2 | 11/2006 | Bedard |
| 7,147,667 B2 | 12/2006 | Bedard |
| 7,164,967 B2 | 1/2007 | Etienne-Cummings et al. |
| 7,190,096 B2 | 3/2007 | Blanding et al. |
| 7,431,737 B2 | 10/2008 | Ragnarsdottir et al. |
| 7,531,006 B2 | 5/2009 | Clausen et al. |
| 7,637,959 B2 | 12/2009 | Clausen et al. |
| 7,888,846 B2 | 2/2011 | Ohtera et al. |
| 7,896,927 B2 | 3/2011 | Clausen et al. |
| 7,898,121 B2 | 3/2011 | Ramsay et al. |
| 7,949,429 B2 | 5/2011 | Ohtera et al. |
| 8,048,172 B2 * | 11/2011 | Jonsson et al. ................ 623/24 |
| 8,057,550 B2 | 11/2011 | Clausen et al. |
| 2002/0043880 A1 | 4/2002 | Suzuki et al. |
| 2002/0087213 A1 | 7/2002 | Bertram |
| 2002/0087216 A1 | 7/2002 | Atkinson et al. |
| 2002/0183803 A1 | 12/2002 | Fang et al. |
| 2002/0198604 A1 | 12/2002 | Schulman et al. |
| 2003/0029247 A1 | 2/2003 | Biedermann |
| 2003/0067245 A1 | 4/2003 | Pelrine et al. |
| 2003/0093158 A1 | 5/2003 | Phillips et al. |
| 2003/0120353 A1 | 6/2003 | Christensen |

(56) References Cited

U.S. PATENT DOCUMENTS

| | | |
|---|---|---|
| 2004/0049290 A1 | 3/2004 | Bedard |
| 2004/0054423 A1 | 3/2004 | Martin |
| 2004/0064195 A1 | 4/2004 | Herr |
| 2004/0088057 A1 | 5/2004 | Bedard |
| 2004/0111163 A1 | 6/2004 | Bedard et al. |
| 2004/0181289 A1 | 9/2004 | Bedard |
| 2004/0193286 A1 | 9/2004 | Grundei |
| 2004/0267379 A1 | 12/2004 | Pasolini |
| 2005/0004495 A1 | 1/2005 | Goswami |
| 2005/0010139 A1 | 1/2005 | Aminian et al. |
| 2005/0107889 A1 | 5/2005 | Bedard et al. |
| 2005/0119763 A1 | 6/2005 | Christensen |
| 2005/0143838 A1 | 6/2005 | Collier |
| 2005/0192677 A1 | 9/2005 | Ragnarsdottir et al. |
| 2005/0197717 A1 | 9/2005 | Ragnarsdottir et al. |
| 2005/0283257 A1 | 12/2005 | Bisbee, III et al. |
| 2006/0041321 A1 | 2/2006 | Christensen |
| 2006/0064195 A1 | 3/2006 | Kern et al. |
| 2006/0122710 A1 | 6/2006 | Bedard |
| 2006/0122711 A1 | 6/2006 | Bedard et al. |
| 2006/0136072 A1 | 6/2006 | Bisbee, III et al. |
| 2006/0155385 A1 | 7/2006 | Martin |
| 2006/0224246 A1 | 10/2006 | Clausen et al. |
| 2006/0224247 A1 | 10/2006 | Clausen et al. |
| 2006/0249315 A1 | 11/2006 | Herr et al. |
| 2007/0016329 A1 | 1/2007 | Herr et al. |
| 2007/0027555 A1 | 2/2007 | Palmer et al. |
| 2007/0027557 A1 | 2/2007 | Jonsson et al. |
| 2007/0043449 A1 | 2/2007 | Herr et al. |
| 2007/0050045 A1 | 3/2007 | Clausen et al. |
| 2007/0123997 A1 | 5/2007 | Herr et al. |
| 2007/0162152 A1 | 7/2007 | Herr et al. |
| 2008/0122303 A1 | 5/2008 | Santo et al. |
| 2010/0113980 A1 | 5/2010 | Herr et al. |
| 2010/0114329 A1 | 5/2010 | Casler et al. |
| 2010/0174384 A1 | 7/2010 | Herr et al. |
| 2010/0174385 A1 | 7/2010 | Casler et al. |
| 2010/0179668 A1 | 7/2010 | Herr et al. |
| 2010/0262260 A1 | 10/2010 | Bedard et al. |
| 2011/0082566 A1 | 4/2011 | Herr et al. |
| 2012/0078380 A1 | 3/2012 | Jonsson et al. |

FOREIGN PATENT DOCUMENTS

| | | |
|---|---|---|
| EP | 1 166 726 | 1/2002 |
| EP | 1 169 982 | 1/2002 |
| FR | 2 623 086 | 5/1989 |
| GB | 2 201 260 | 8/1988 |
| GB | 2 244 006 | 11/1991 |
| GB | 2 260 495 | 4/1993 |
| GB | 2 301 776 | 12/1996 |
| GB | 2 302 949 | 2/1997 |
| GB | 2 367 753 | 8/1998 |
| GB | 2 338 653 | 12/1999 |
| JP | 11-056885 | 3/1999 |
| JP | 11000345 | 6/1999 |
| JP | 2001-277175 | 10/2001 |
| JP | 2002-191654 | 7/2002 |
| WO | WO 94/06374 | 3/1994 |
| WO | WO 95/26171 | 10/1995 |
| WO | WO 96/41599 | 12/1996 |
| WO | WO 97/00661 | 1/1997 |
| WO | WO 98/38951 | 9/1998 |
| WO | WO 99/05991 | 2/1999 |
| WO | WO 00/27318 | 5/2000 |
| WO | WO 01/17466 | 3/2001 |
| WO | WO 03/003953 | 1/2003 |

OTHER PUBLICATIONS

Blaya, J. A., et al., "Adaptive Control of a Variable-Impedance Ankle-Foot Orthosis to Assist Drop-Foot Gait" IEEE Transactions on Neural Systems and Rehabilitation Engineering, vol. 12, No. 1, Mar. 2004, pp. 24-31.

Copes, Bionic Ankle: The Most Significant Development in Ankle Prosthetics in Over a Half Century, 1985, 3 pages, USA.

Flowers, et al., Journal of Biomechanical Engineering: Transactions of the ASME; Feb. 1977, pp. 3-8.

H. Dietl & H. Bargehr, Der Einsatz von Elektronik bei Prothesen zur Versorgung der unteren Extremitat, Med. Orth. Tech., 1997, pp. 31-35, vol.-issue 117, Gentner Verlag Stuttgart, Austria.

PCT International Search Report and Written Opinion mailed Aug. 19, 2005, Appl. No. PCT/US2005/004878 (OSSUR.053VPC), 15 pages.

Proteor, Assembly and Adjustment Instructions for 1P50-R, Sep. 2004, pp. 1-21, France.

Suga, T., et al., "Newly designed computer controlled knee-ankle-foot orthosis (Intellegent Orthosis)", Prostetics and Orthotics International, 1998, 22, 230-239.

Townsend M A et al., "Biomechanics and modeling of bipedal climbing and descending." Journal of Biomechanics 1976, vol. 9, No. 4, pp. 227-239, XP008078405.

* cited by examiner

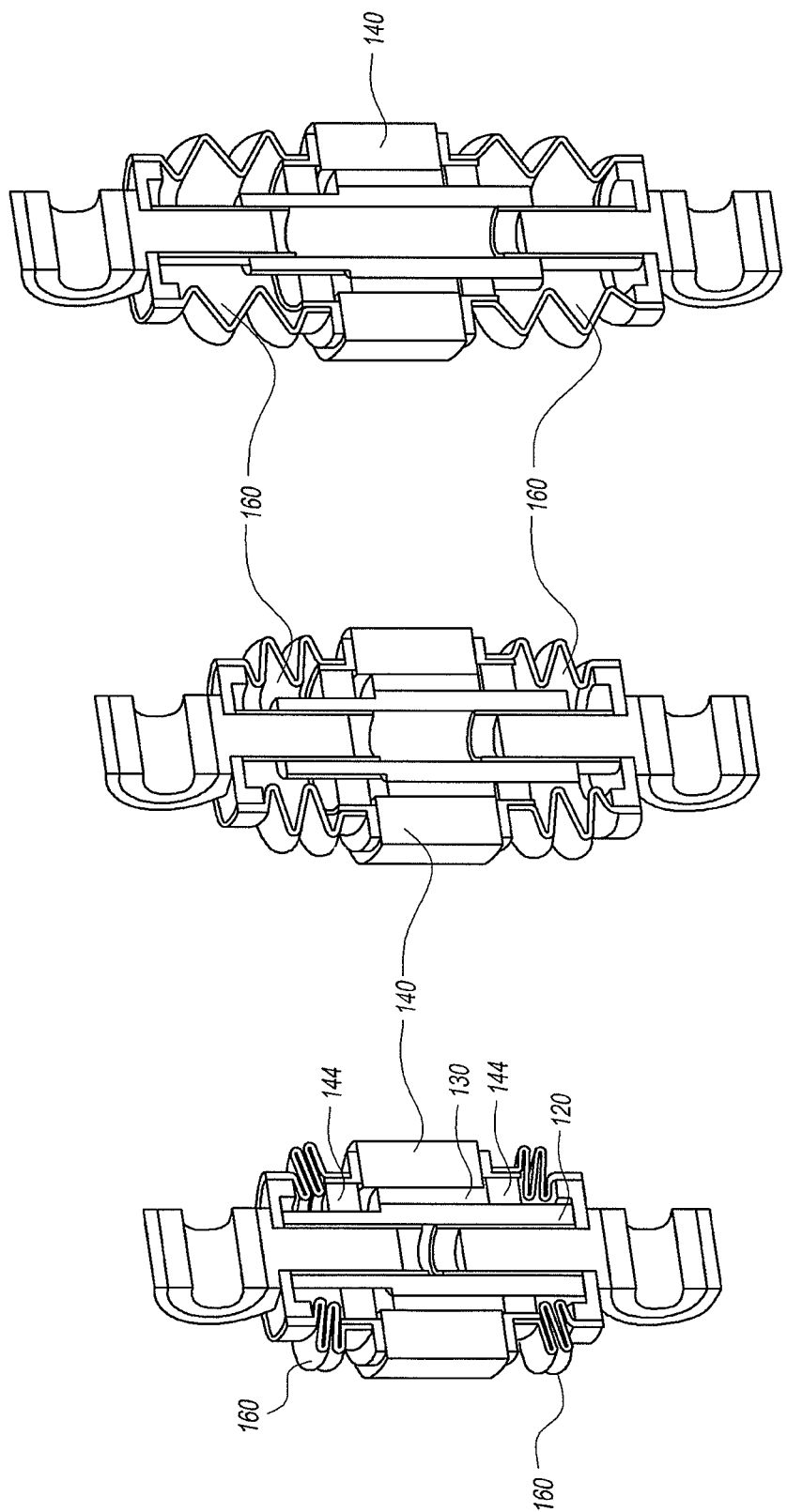

LINEAR ACTUATOR

CROSS-REFERENCE TO RELATED APPLICATIONS

The present application claims priority benefit of U.S. Provisional Application No. 61/609,080, filed Mar. 9, 2012, the entirety of which is incorporated by reference herein and should be considered part of this specification.

BACKGROUND

1. Field

The present application relates to linear actuators, and more particularly, to linear actuators used in prosthetic or orthotic joints.

2. Description of the Related Art

Various types of prosthetic devices are available as artificial substitutes for a missing body part, such as an arm or leg. Prosthetic joints are also available as substitutes for human joints, such as an ankle or knee. Prosthetic joints can include linear actuators to create motion of the joint.

Screw type linear actuators include a screw threadingly coupled to a rotating nut or rotor and function by translating rotation of the nut into linear motion of the screw. The interaction of the threads of the screw and nut can generate a friction force that inhibits rotation of the screw and nut relative to each other. Thus, the actuator can be self-locking under certain conditions, particularly when loaded.

A disadvantage of such actuators is the difficulty in balancing a desired locking force with a desired speed of linear displacement during motion. Screws with smaller pitches generally provide better self-locking properties. However, reducing the thread pitch also reduces the speed of linear motion because a smaller pitch results in a smaller axial displacement of the screw per rotation of the nut.

SUMMARY

The actuator described herein advantageously provides improved self-locking properties without sacrificing axial response.

In some embodiments, an actuator includes an electric motor having stator windings, an elongate rotor, first and second screws, and an elongate magnet. The elongate rotor has an upper internally threaded portion and a lower internally threaded portion. The first and second screws extend along a longitudinal axis of the actuator from opposite sides of the motor. The first screw has a first externally threaded portion to operatively engage the upper internally threaded portion of the rotor, and the second screw has a second externally threaded portion to operatively engage the lower internally threaded portion of the rotor. The second screw is configured to move along the longitudinal axis of the actuator relative to the motor. The elongate magnet is operatively coupled to the rotor and radially interposed between the first and second screws and the motor. The motor is disposed circumferentially about at least a portion of the rotor and first and second screws and is configured to axially displace one or both of the first and second screws via the magnet.

In some embodiments, an actuator includes an electric motor having stator windings, an elongate rotor, at least one screw, and an elongate magnet. The elongate rotor has at least one internally threaded portion, and the at least one screw has an externally threaded portion to operatively engage the at least one internally threaded portion of the rotor. The elongate magnet is operatively coupled to the rotor and radially interposed between the at least one screw and the motor. The magnet is not axially fixed with respect to the motor. The motor is disposed circumferentially about at least a portion of the rotor and at least one screw and is configured to axially displace at least one of the at least one screw and the rotor via the magnet.

In some embodiments, a device configured to be attached to a limb includes a first portion, a second portion, and an actuator. The first and second portions are pivotable relative to each other (e.g., to simulate the movement of a natural human joint). The actuator includes an electric motor comprising stator windings, an elongate rotor, first and second screws, and an elongate magnet. The elongate rotor has an upper internally threaded portion and a lower internally threaded portion. The first and second screws extend along a longitudinal axis of the actuator from opposite sides of the motor. The first screw has a first externally threaded portion to operatively engage the upper internally threaded portion of the rotor, and the second screw has a second externally threaded portion to operatively engage the lower internally threaded portion of the rotor. The second screw is configured to move along the longitudinal axis of the actuator relative to the motor. The elongate magnet is operatively coupled to the rotor and radially interposed between the first and second screws and the motor. The magnet is not axially fixed with respect to the motor. The motor is disposed circumferentially about at least a portion of the rotor and at least one screw and is configured to axially displace at least one of the at least one screw and the rotor via the magnet to adjust an angle between the first portion and the second portion.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIGS. 1A-2C show cross sectional views of example embodiments of an actuator;

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Figure 1:
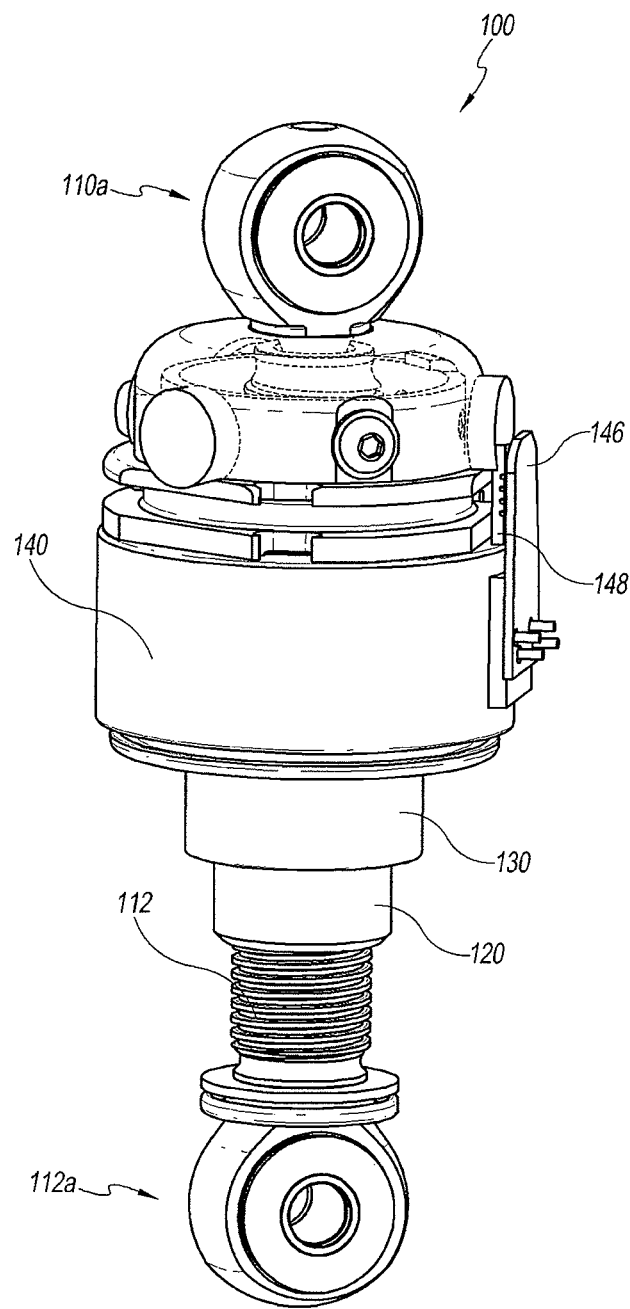
FIG. 1 shows a perspective view of an example embodiment of an actuator.
Figure 1A:
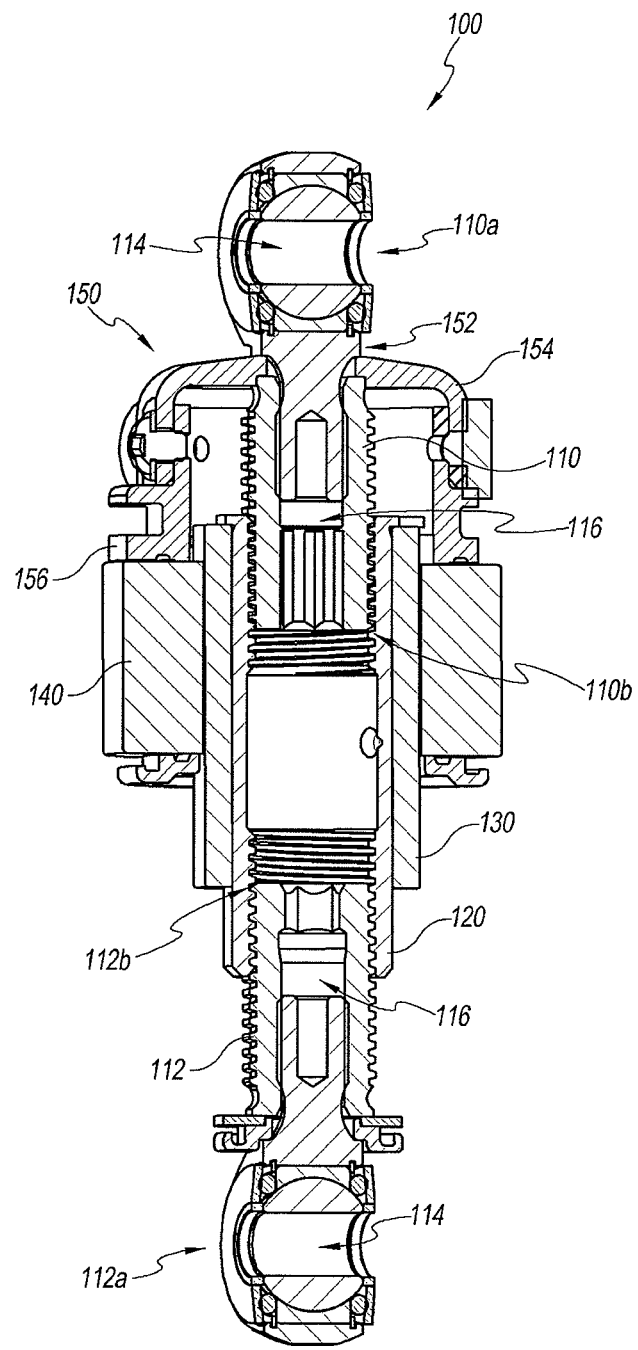

With reference to FIGS. 1 and 1A, an example embodiment of a linear actuator 100 includes two screws—an upper screw 110 and lower screw 112, an elongate nut 120, an elongate magnet ring 130, and a stator 140 having one or more coils. The upper 110 and lower 112 screws extend from opposite ends of the actuator 100. Each screw 110, 112 has a head 110a, 112a and an end 110b, 112b at opposite ends of the screw 110, 112. The heads 110a, 112a are oriented at the top and bottom, respectively, of the actuator 100, and the ends 110b, 112b are disposed opposite each other along a longitudinal axis (e.g., central axis or symmetrical axis) of the actuator 100. In one embodiment, one screw can have clockwise threads while the other has counter-clockwise threads.

The nut 120, which acts as a rotor, is generally cylindrical and disposed around and operatively coupled to the screws 110, 112. The nut 120 extends along a length between the screw heads 110a, 112a. In some embodiments, the nut 120 has an upper internally threaded portion sized and shaped to engage the upper screw 110 and a lower internally threaded portion sized and shaped to engage the lower screw 112. The threads of the screws 110, 112 threadingly engage the internally threaded portions of the nut 120. Rotation of the nut 120 is translated into linear motion of the screws 110, 112 relative to the nut 120 and causes the distance between the ends 110b, 112b of the screws 110, 112 to increase or decrease, depending on the direction of rotation. Because rotation of the nut 120 causes axial displacement of both screws 110, 112, each rotation of the nut 120 advantageously causes greater total axial movement compared to an actuator having a single screw. This also allows for the use of screws 110, 112 having smaller pitches to enhance the self-locking properties of the actuator without sacrificing axial displacement capabilities.

In some embodiments, the threads of the screws 110, 112 and nut 120 can be trapezoidal threads. However, any suitable thread type can be used. The pitch, material, working diameter, and other characteristics of the screws 110, 112 can be selected to promote self-locking when the actuator 100 is loaded (e.g., when a load is applied to the actuator via the screw heads 110a, 112a), so as to inhibit axial movement of the screws 100, 112 or rotation of the nut 120 when the actuator 100 is loaded. The self-locking capacity of a screw is a function of a helix angle or inclination of the threads, which is a function of both the screw pitch and diameter. For example, a larger diameter screw has a smaller helix angle than a smaller diameter screw having the same pitch and therefore has increased self-locking force potential. For another example, selecting a smaller pitch for a screw having a particular diameter can also help increase the self-locking force potential.

Figure 1B:
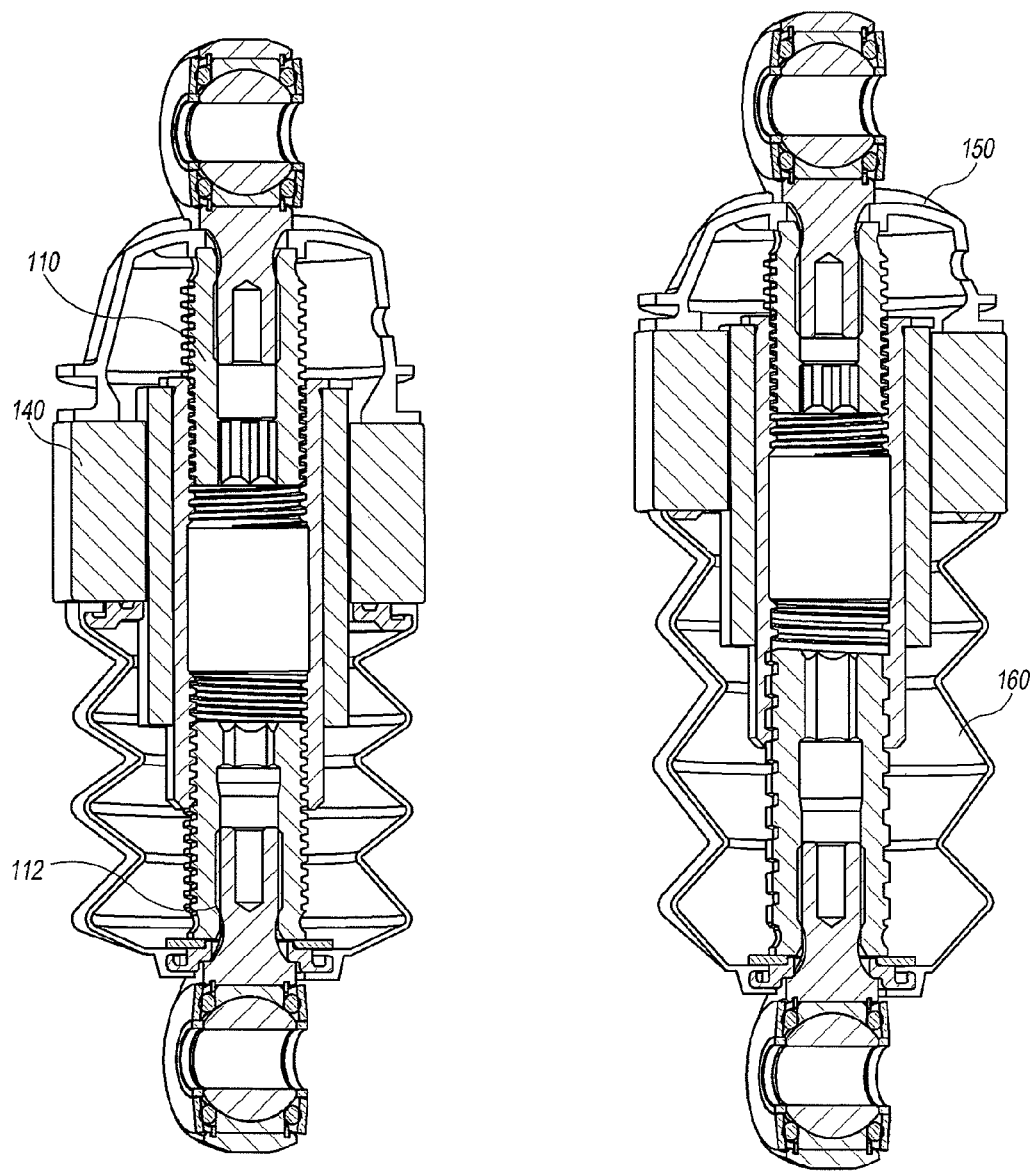

In some embodiments, the screws 110, 112 can have threads of different pitches. Such an arrangement can help achieve a desired balance between the locking force and speed of linear displacement. For example, one screw can have threads of a smaller pitch to increase the self-locking force, while the other screw can have threads of a larger pitch to provide greater axial displacement during motion. In some embodiments, the screws 110, 112 can have different diameters, for example as shown in FIG. 1B. This can help allow for easier construction as a screw with a larger pitch often requires a larger diameter. In some embodiments, the screws 110, 112 have hollow portions 116 to advantageously reduce the weight of the screws 110, 112 and therefore the actuator 100 as a whole.

The elongate magnet ring 130 circumferentially surrounds and is coupled to the nut 120. The stator 140, in turn, is disposed around the magnet 130. The stator 140 can include stator windings or coils that act as an electric motor for the actuator 100. In one embodiment, the stator 140 and magnet 130 are spaced apart from each other by a radial gap. In operation, the motor rotates the nut 120 via the magnet 130. The motor can be a stepper motor, DC motor, piezo-electric motor, DC brushless motor, servo motor, or any other suitable motor. In some embodiments, the nut 120 and magnet 130 are not axially fixed and can move axially relative to the stator 140. Thus, the nut 120 can rotate about and translate along the longitudinal axis of the actuator, while the screws 110, 112 are rotationally fixed (e.g., via the coupling of the heads 110a, 112a to other members) but can translate along the longitudinal axis of the actuator 100. In some such embodiments, the magnet 130 is longer than magnets in traditional actuators to allow for axial movement of the rotor nut 120 relative to the stator 140.

Figure 1C:
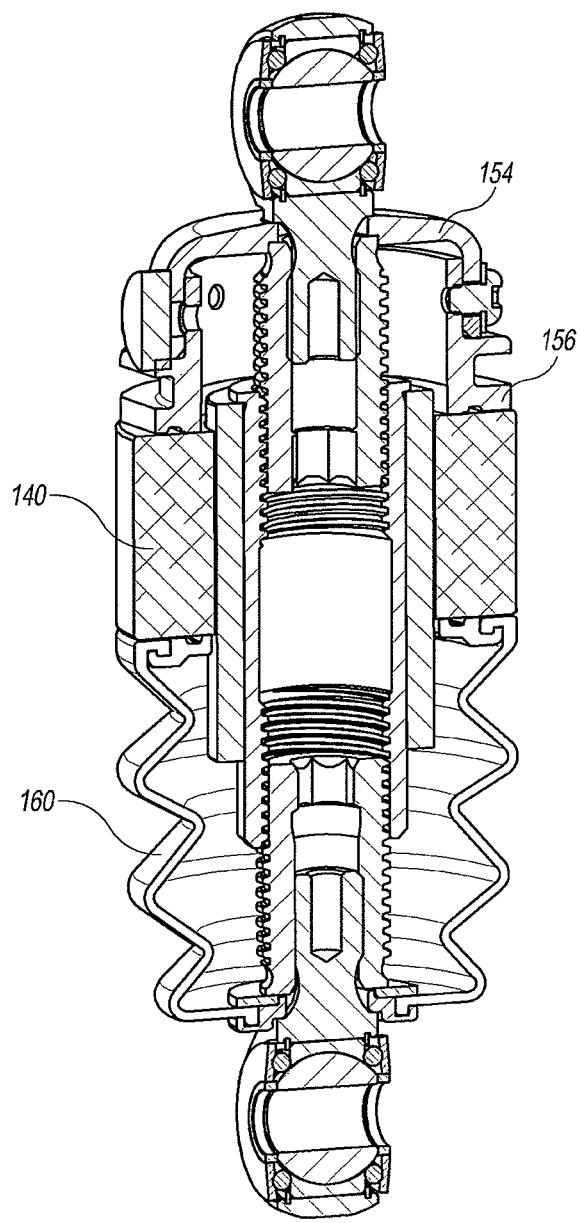

In some embodiments, the upper screw 110 is coupled to, e.g., bolted through, a stator fixture 150 at 152. The stator fixture 150 can include two components, a top component 154 and a bottom component 156, for example as shown in FIG. 1C, and can be generally rigid or have limited flexibility. In another embodiment, the stator fixture 150 can be resilient. The bottom of the stator fixture can be fixedly coupled to the stator 140, so the upper screw 110 is fixed axially and rotationally relative to the stator 140, and neither the upper screw 110 nor stator 140 rotate or move axially in operation. This configuration advantageously helps maintain the radial air gap between the magnet 130 and stator 140 and prevents the stator 140 from rotating. In operation, the nut 120 can move axially relative to the stator 140, and the lower screw 112 can move axially relative to the nut 120. This design advantageously does not require bearings or bushings, for example between the rotor 120 and stator 140. Therefore, in some embodiments, the only friction surfaces in the actuator 100 are the threads of the screws 110, 112 and the rotor nut 120.

In some embodiments, the stator 140 is not axially fixed in operation and can move along the longitudinal axis of the actuator 100, for example as shown in FIGS. 2A-2C. Ball bearings can support the stator 140 over the rotor 120 so that the stator 140 can move axially with the rotor 120. In the illustrated embodiment, ball bearings 144 are disposed at the proximal and distal ends of the stator 140 and interconnect the stator 140 to the rotor 120. Bellows 160 extend between the proximal and distal ends of the stator 140 and the upper and lower screw heads 110a, 112a.

In some embodiments, for example as shown in FIGS. 1B, 1C, and 2A-2C, the actuator 100 can include a bellows 160 circumferentially surrounding a portion of the actuator 100. The bellows 160 can extend from a bottom of the stator 140 to the lower screw 112 head 112a. In some embodiments, as shown in FIGS. 2A-2C, a bellows 160 can also extend from a top of the stator 140 to the upper screw 110 head 110a. The bellows 160 can advantageously help protect the actuator 100 components from the entry of foreign particles, such as dust and water.

Figure 3:
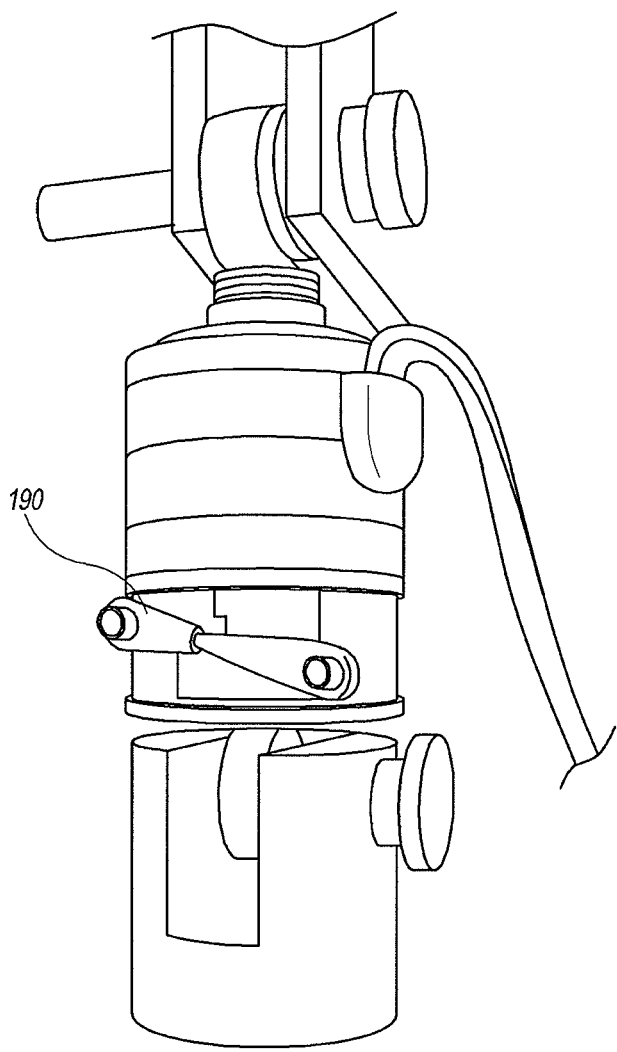
FIG. 3 illustrates an example embodiment of an actuator having a pair of control arms.

In some embodiments, the actuator 100 can include a mechanism to control rotation of the stator 140 during use. For example, the actuator 100 can include one or more control arms 190 as shown in FIG. 3. One control arm 190 is visible in FIG. 3; however, the actuator 100 can include another control arm 190 on the opposite side of the actuator 100. In some embodiments, the one or more control arms 190 can be provided in place of the bellows to interconnect, for example, the stator 140 with one or both of the upper screw 110 and lower screw 112 to allow relative movement between the stator 140 and the screws 110, 112. In some embodiments in which the stator 140 is not axially fixed in operation, the one or more control arms 190 can inhibit or prevent rotation of the stator 140 while allowing axial displacement of the stator 140.

Figure 4A:
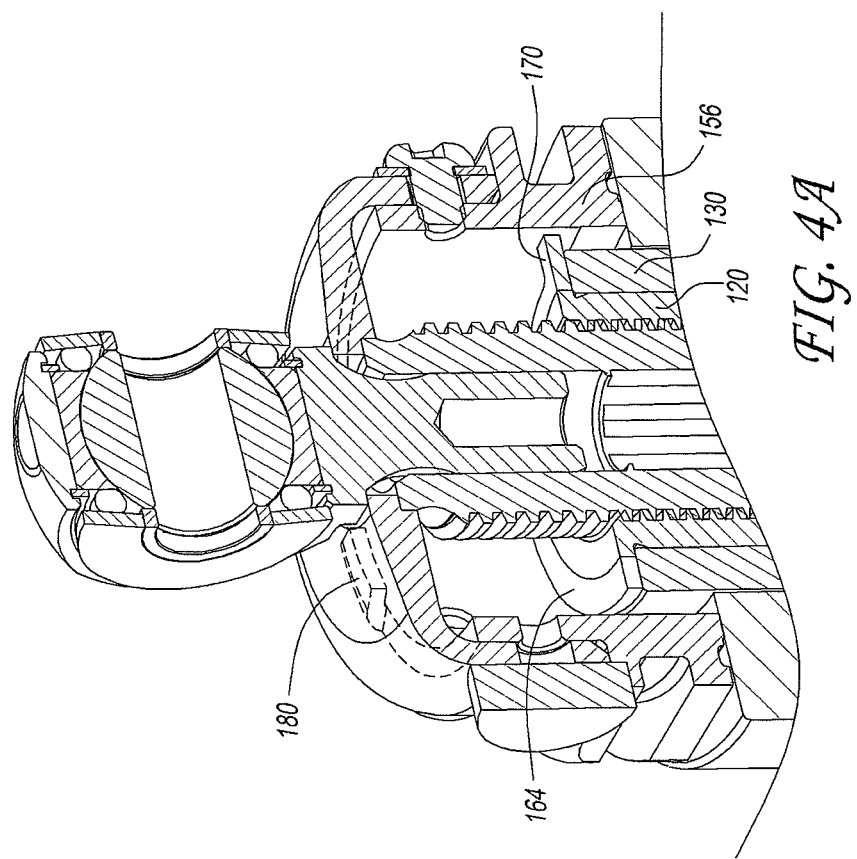
FIGS. 4A-4F show example embodiments of a mechanism for limiting the range of motion of an actuator.
Figure 4B:
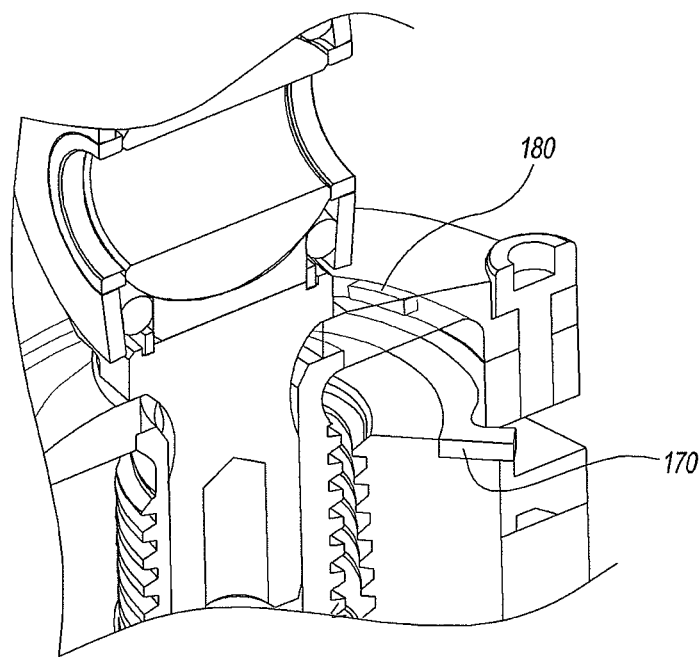
Figure 4C:
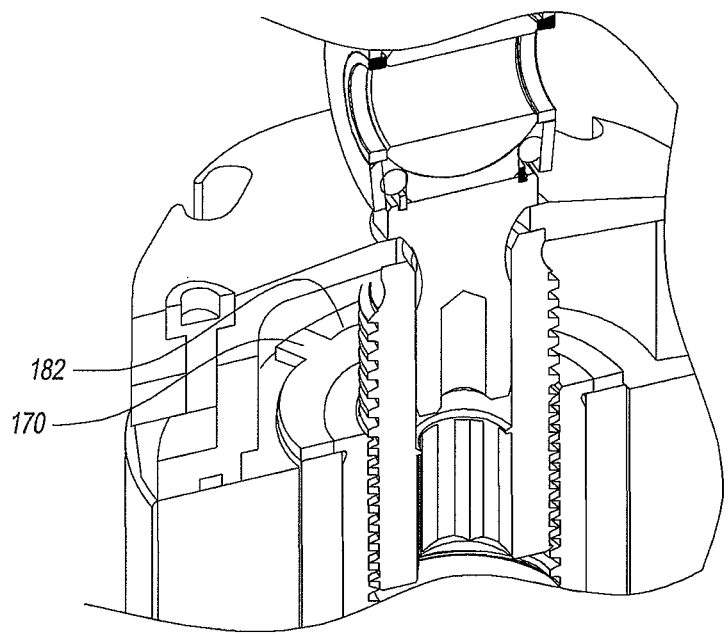
Figure 4D:
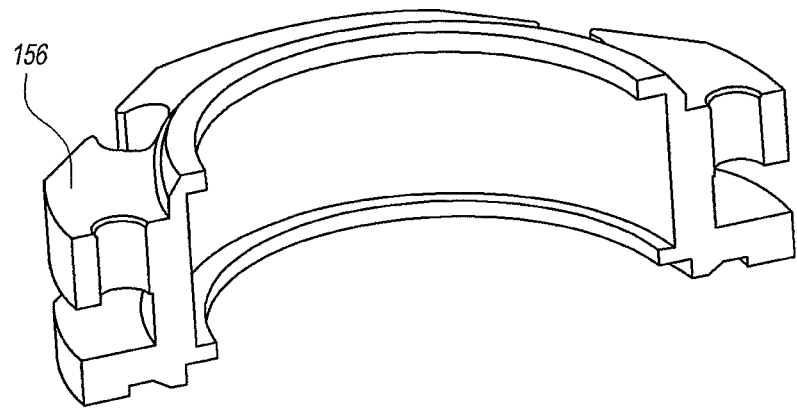
Figure 4E:
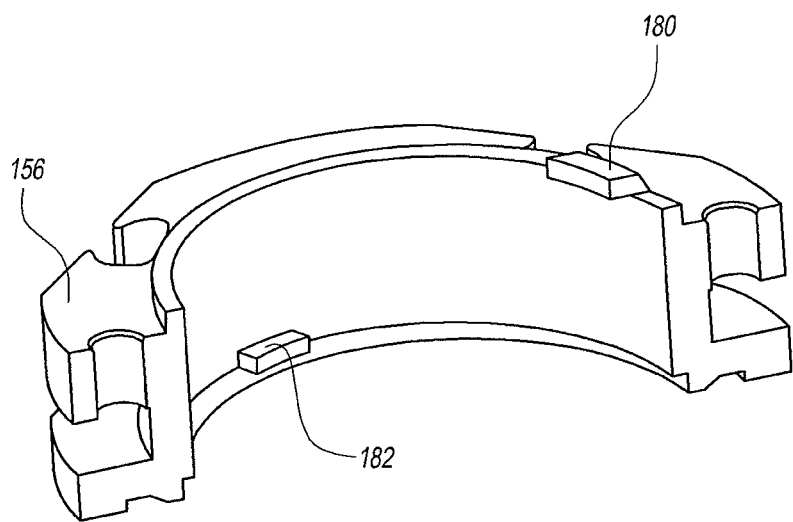
Figure 4F:
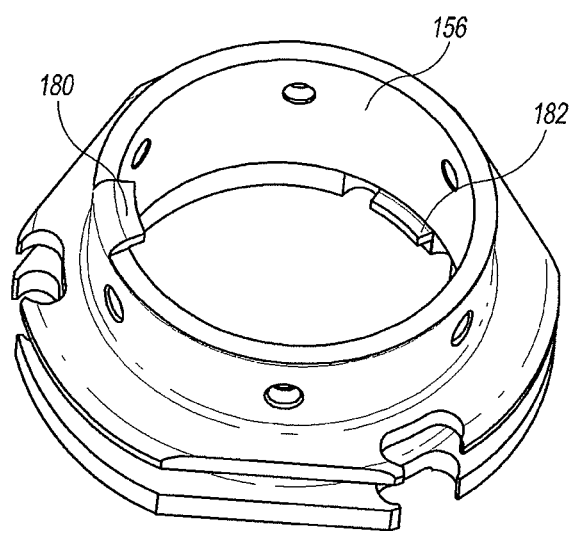

In some embodiments, the actuator 100 can include a mechanism to limit the range of motion of the actuator 100 during use. In some embodiments, the stator fixture 150 and nut 120-magnet 130 assembly can include corresponding features that act to limit the range of motion of the actuator 100 during use, for example as shown in FIGS. 4A-4E. A top surface 164 of the nut 120-magnet 130 assembly can include an outwardly extending tab 170 as shown in FIGS. 4A-4C. The top surface 164 and/or tab 170 can be integrally formed with, machined into, or coupled to the nut 120-magnet 130 assembly. The stator fixture 150 or bottom component 156 of the stator fixture 150 can include corresponding end stops 180, 182 configured to contact the tab 170. The end stops 180, 182 can be integrally formed with, machined into, or coupled to the stator fixture 150. FIG. 4D illustrates an example embodiment of the bottom component 156 of the stator fixture 150 before the end stops 180, 182 are machined or otherwise formed, and FIG. 4E shows the bottom component 156 including the upper end stop 180 and lower end stop 182. FIG. 4F illustrates another example embodiment of the bottom component 156 including the upper end stop 180 and lower end stop 182. In use, when the actuator 100 is functioning so that the ends 110b, 112b of the screws 110, 112 are moving towards one another and the actuator 100 reaches a minimum length, the tab 170 will contact the upper end stop 180. When the ends 110b, 112b of the screws 110, 112 are moving away from each other and the actuator 100 reaches a maximum length, the tab 170 will contact the lower end stop 182 as shown in FIG. 4C. This design can advantageously allow for the end stops to function even under high speed and/or momentum conditions of the rotor 120.

Figure 5:
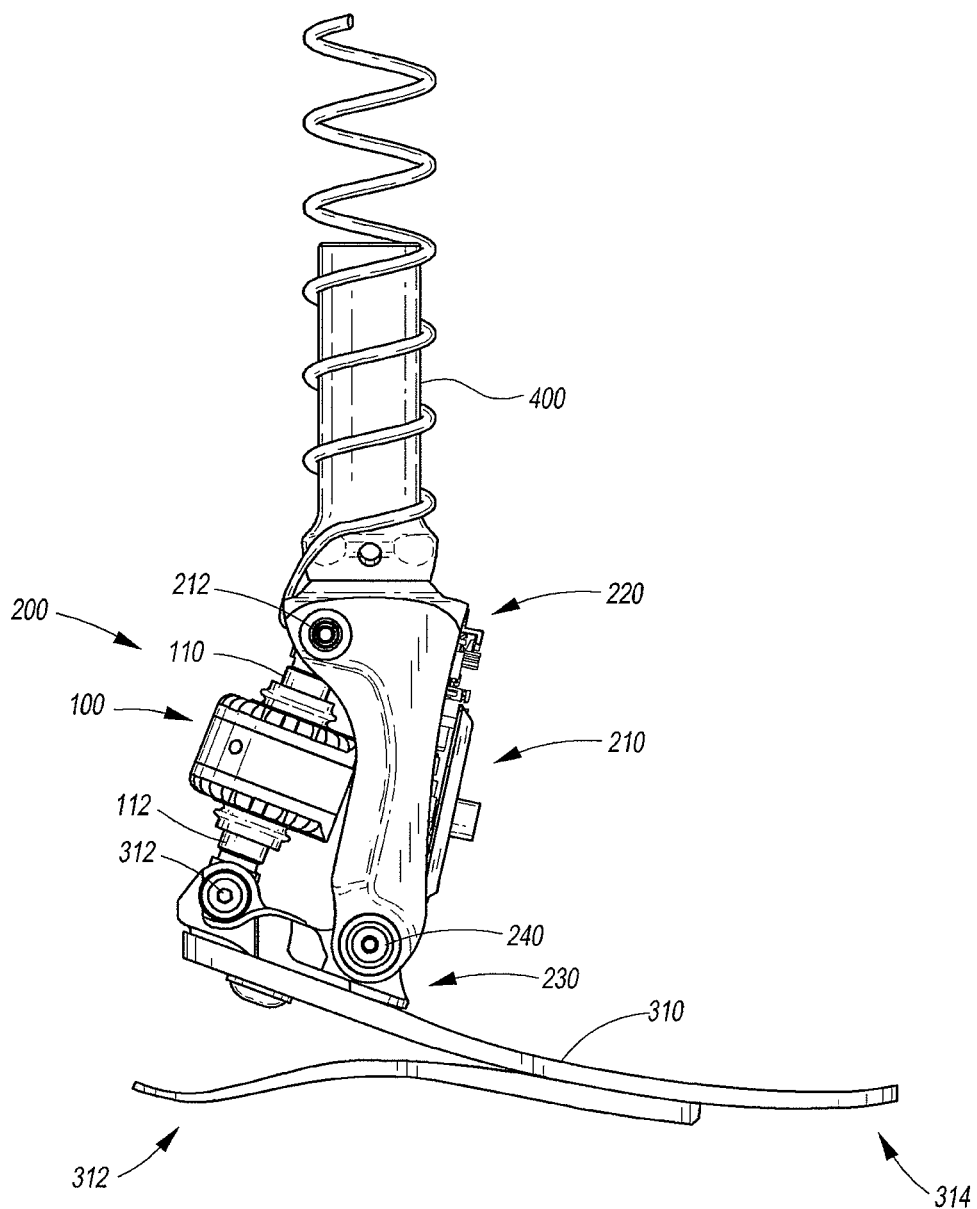
FIG. 5 shows an example embodiment of an actuator used in a prosthetic ankle joint.

In some embodiments, an actuator 100 as described herein can be used in a prosthetic joint, for example, a prosthetic ankle 200 as shown in FIG. 5. When used in a prosthetic joint, the screw heads 110a, 112a can include attachment portions to couple the actuator 100 to other prosthetic components. The screw heads 110a, 112a, which in some embodiments can include spherical bearings, can have openings 114 therethrough aligned along an axis that extends generally perpendicular to a longitudinal axis of the actuator 100. The openings 114 can be sized to receive a fastener therethrough, such as a bolt, screw, pin, or axle, to allow for attachments to other components. However, the attachment portions can have other suitable configurations.

In the illustrated embodiment, the upper screw head 110a can be coupled to a proximal end 220 of a lower limb member 210 at upper attachment point 212 (e.g., via a pin, axle, etc.), and the lower screw head 112a can be coupled to a prosthetic foot 310 at lower attachment point 312 to form a lower limb prosthesis 200. A distal end 230 of the lower limb member 210 can be coupled to the prosthetic foot 310 via a pivot 240 near the location of a natural human ankle. The proximal end 220 of the lower limb member 210 can be coupled to another prosthetic component, for example, a socket connector attached to the user's stump or to a pylon 400 as shown in FIG. 5.

Figure 6:
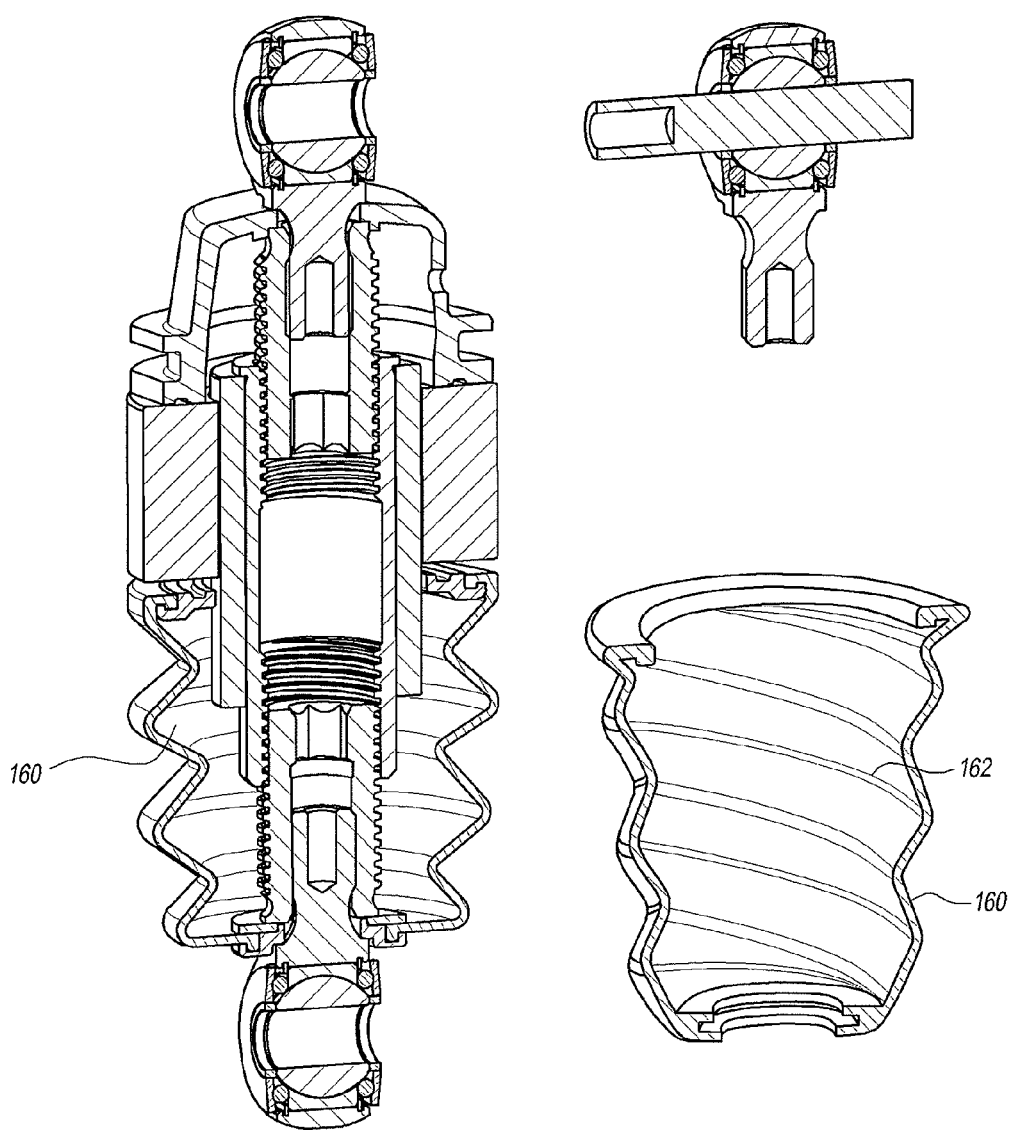
FIG. 6 shows an example embodiment of an actuator and bellows.

As discussed herein, the actuator 100 can include a bellows 160 circumferentially surrounding a bottom portion of the actuator 100. In some embodiments, the bellows 160 can include a spring 162 as shown in FIG. 6 to help balance the weight of the foot assembly 310 around a prosthetic ankle pivot axis. This can allow the actuator 100 to produce more force for toe lift of the prosthetic foot. In the illustrated embodiment, the spring 162 can have a helical design. However, in other embodiments, the spring 162 can have other suitable designs, such as a tapered design. Corrugations of the bellows 160 can be shaped to correspond to the shape of the spring 162 used. A tapered design can provide the benefits of a better fit and a smaller compressed height compared to a helical design. Alternatively, in some embodiments, the actuator 100 can include a torsion spring along a longitudinal axis. A torsion spring may provide a more constant torque to help balance the weight of the foot assembly. In some embodiments, other mechanisms can be used to help balance the weight of the foot assembly 310.

Figure 7A:
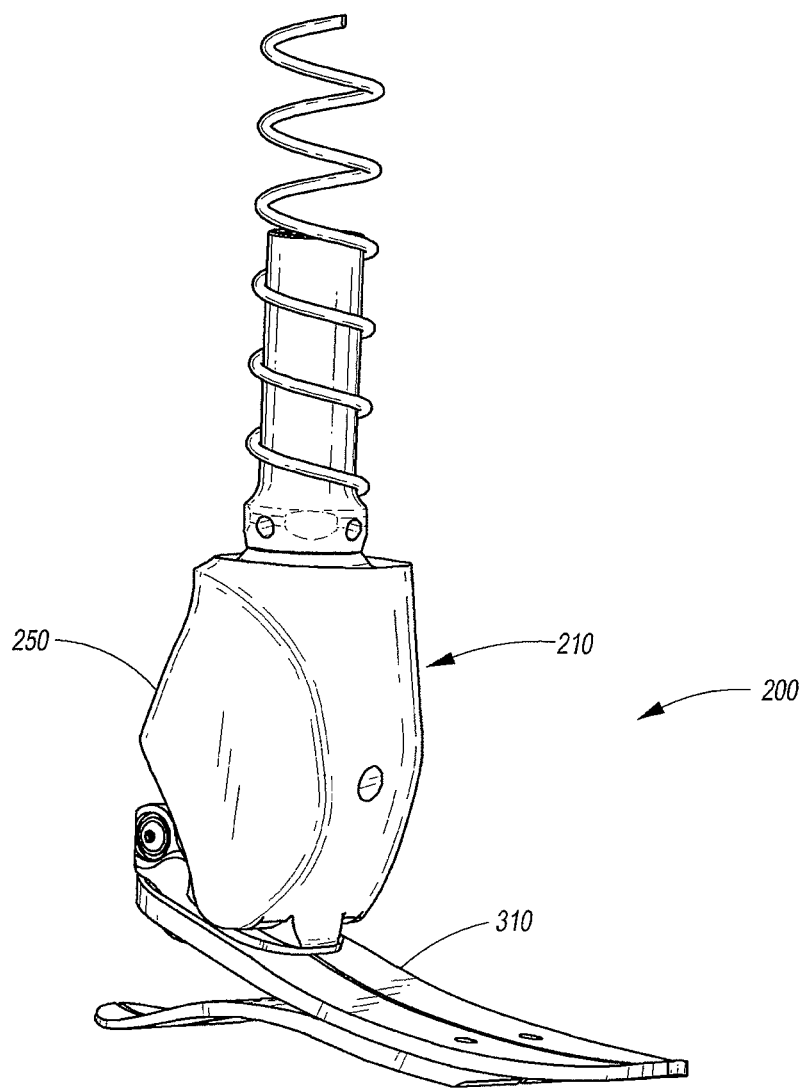
FIG. 7A shows the ankle joint of FIG. 5 including a cover.
Figure 7B:
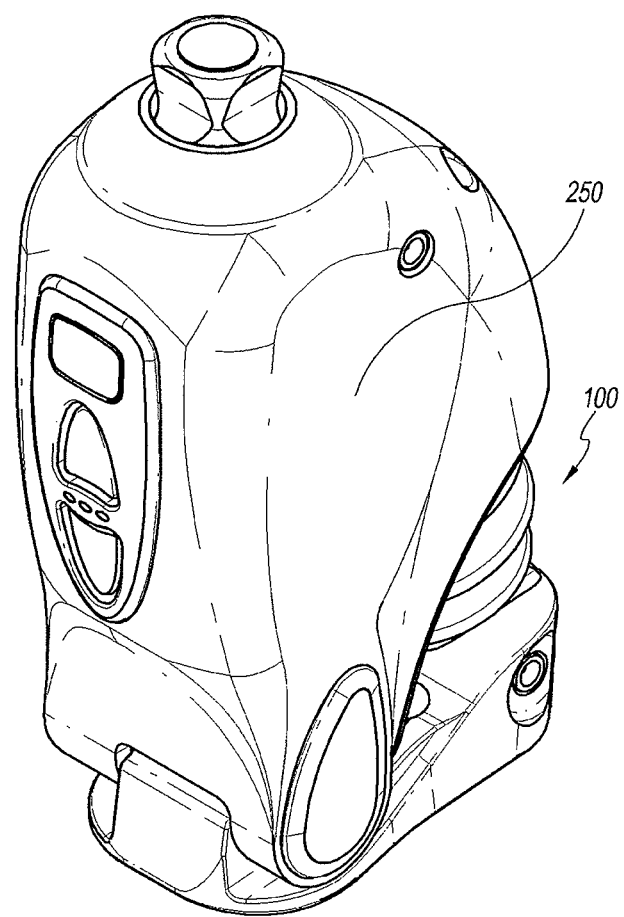
FIG. 7B shows an example embodiment of a cover for an actuator used in a prosthetic ankle joint.

In some embodiments, as shown in FIGS. 7A and 7B, the lower limb member 210 includes a cover 250 to protect the inner components of the lower limb member 210 and/or actuator 100. In some embodiments, the cover 250 can be shaped in the form of a natural human leg. The prosthetic foot 310 can be various types of prosthetic feet. In some embodiments, the prosthetic foot 310 can include a cosmesis or foot cover to protect the foot 310 and give the appearance of a natural human foot.

When used in a prosthetic ankle, the linear actuator 100 can cause the prosthetic foot 310 to move similarly to a natural human foot. In use, the actuator 100 adjusts an angle between the prosthetic components by pushing or pulling a posterior portion of the lower limb member 210 and/or prosthetic foot 310 (e.g., adjusting an angle between the lower limb member 210 and the prosthetic foot 310). The actuator 100 can be self-powered to advantageously reduce the energy expenditure required on the part of the user. For example, the lower limb prosthesis 200 can include a battery to provide power to the actuator 100 and/or other components of the system (e.g., processor and/or electronic controller, one or more sensors, a memory module, etc.). In some embodiments, the actuator 100 can also selectively lock and unlock during certain phases of the gait cycle. For example, the linear actuator 100 can provide axial movement during the swing phase of the user's gait cycle, thereby simulating muscular function. During stance, the linear actuator can act as an Achilles tendon to maintain the ankle at a fixed position until the foot is free from the ground. In other embodiments, the actuator 100 can actuate during the stance and/or swing phases to vary the angle between the lower limb member 210 and the prosthetic foot 310. Additionally, the actuator 100 can actuate based at least in part on one or more sensed characteristics of the prosthetic foot 310 (e.g., force, moment, ankle angle).

In one embodiment, when a user is standing still, the user's weight loads the actuator 100 and the self-locking properties of the actuator 100 prevent rotation of the screws 110, 112. The actuator 100 therefore maintains the orientation of the ankle at a substantially fixed position and inhibits (e.g., prevents) a change in the angle between the lower limb member 210 and foot 310 for user stability. When the user is walking, the user progresses through various phases of a gait cycle, including heel strike, mid-stance, toe-off, and swing. During swing, the actuator 100 is unloaded, so the nut 120 is free to rotate and the actuator 100 can operate to adjust the angle between the lower limb member 210 and foot 310. Additional information regarding example actuators used in prosthetic joints and their operation during a user's gait cycle, among other things, can be found in U.S. Pat. No. 8,048,172, the entirety of which is hereby incorporated by reference for all purposes and should be considered a part of this specification.

The actuator 100 described herein can also allow the lower limb member 210 and/or foot 310 to adjust to inclines and declines. To adapt to an incline, the motor rotates the nut 120 via the magnet 130 in a direction so that the distance between the ends 110b, 112b of the screws 110, 112 increases and causes the angle between the lower limb member 210 and foot 310 to decrease. This is dorsiflexion of the foot 310. To adapt to a decline, the motor rotates the nut 120 via the magnet 130 in the opposite direction so that the distance between the ends 110b, 112b of the screws 110, 112 decreases and causes the angle between the lower limb member 210 and foot 310 to increase. This is plantarflexion of the foot 310. The actuator 100 can advantageously accommodate level ground walking, travel up and down stairs, and travel on uneven or different terrain. The actuator 100 can also allow for heel height adjustability, for example through the user pressing one or more buttons or automatically. In some embodiments, the lower limb prosthesis 200 includes a sensor system and/or a control system to manage motion of the prosthesis 200, for example as described in U.S. Pat. No. 8,048,172, which is incorporated by reference herein in its entirety. With reference to FIG. 1, the actuator 100 can include a panel 146 that provides a location for mounting a connector 148 for circuitry associated with such a control system. In some embodiments, the connector 148 receives a motor-cable that controls and/or activates the motor.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. For example, though the actuator 100 is disclosed herein as being incorporated into a lower limb prosthesis 200, and more specifically a prosthetic foot, the actuator 100 can also be incorporated into other prosthetic joints, such as a knee joint, where the upper screw head 110a can be coupled to a prosthetic femoral component and the lower screw head 112a can be coupled to a prosthetic tibial component. In other embodiments, the actuator can be incorporated into devices other than prosthetic or orthotic devices, such as any device (e.g., industrial devices) that uses a linear actuator. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above.

What is claimed is:

1. An actuator, comprising:
   an electric motor comprising stator windings;
   an elongate rotor, the rotor having an upper internally threaded portion and a lower internally threaded portion;
   a first screw that extends along a longitudinal axis of the actuator, the first screw having a first externally threaded portion to operatively engage the upper internally threaded portion of the rotor;
   a second screw that extends along the longitudinal axis of the actuator and is configured to move along the longitudinal axis relative to the motor, the second screw having a second externally threaded portion to operatively engage the lower internally threaded portion of the rotor, the first and second screws extending from opposite sides of the motor; and
   an elongate magnet operatively coupled to the rotor and radially interposed between the first and second screws and the motor;
   wherein the motor is disposed circumferentially about at least a portion of the rotor and first and second screws, the motor configured to axially displace one or both of the first and second screws via the magnet.

2. The actuator of claim 1, wherein a pitch of the first screw is different than a pitch of the second screw.

3. The actuator of claim 1, wherein the first screw is coupled to a stator fixture, the stator fixture coupled to the motor.

4. The actuator of claim 1, wherein the first screw is axially fixed with respect to the motor.

5. The actuator of claim 1, wherein a pitch of at least one of the first and second screws is configured to promote self-locking properties of the actuator.

6. The actuator of claim 1, wherein the magnet and rotor are not axially fixed with respect to the motor.

7. A device configured to be attached to a limb, comprising:
   a first portion;
   a second portion, the first and second portions pivotable relative to each other to simulate movement of a natural human joint; and
   an actuator comprising:
     an electric motor comprising stator windings;
     an elongate rotor, the rotor having an upper internally threaded portion and a lower internally threaded portion;
     a first screw that extends along a longitudinal axis of the actuator, the first screw having a first externally threaded portion to operatively engage the upper internally threaded portion of the rotor;
     a second screw that extends along the longitudinal axis of the actuator and is configured to move along the longitudinal axis relative to the motor, the second screw having a second externally threaded portion to operatively engage the lower internally threaded portion of the rotor, the first and second screws extending from opposite sides of the motor; and
     an elongate magnet operatively coupled to the rotor and radially interposed between the first and second screws and the motor, wherein the magnet is not axially fixed with respect to the motor;
     wherein the motor is disposed circumferentially about at least a portion of the rotor and first and second screws, the motor configured to axially displace one or both of the first and second screws and the rotor via the magnet to adjust an angle between the first portion and the second portion.

8. The device of claim 7, wherein the first portion is a lower limb member.

9. The device of claim 7, wherein the second portion is a prosthetic foot.

10. The device of claim 7, wherein the natural human joint is a natural human ankle.

11. The device of claim 7, wherein the first and second screws have threads of different pitches.

12. The device of claim 7, wherein threads of at least one of the first and second screws are configured to enhance self-locking properties of the actuator.

13. The device of claim 7, wherein actuator is configured to selectively lock and unlock during desired phases of a user's gait cycle.

14. The device of claim 13, wherein the actuator locks during stance.

15. The device of claim 13, wherein the actuator unlocks during swing.

16. The device of claim 7, wherein the first screw is axially fixed with respect to the motor.

* * * * *